United States Patent
Maeda et al.

(10) Patent No.: US 8,999,240 B2
(45) Date of Patent: Apr. 7, 2015

(54) AUTOMATIC ANALYZER

(75) Inventors: Noriko Maeda, Hitachinaka (JP); Kyoko Imai, Hitachinaka (JP); Taku Sakazume, Hitachinaka (JP); Yukie Tokiwa, Hitachinaka (JP); Kantaro Suzuki, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/546,628

(22) Filed: Jul. 11, 2012

(65) Prior Publication Data
US 2012/0282141 A1 Nov. 8, 2012

Related U.S. Application Data

(63) Continuation of application No. 11/514,185, filed on Sep. 1, 2006, now Pat. No. 8,246,907.

(30) Foreign Application Priority Data

Sep. 5, 2005 (JP) ................. 2005-255803

(51) Int. Cl.
*G01N 35/00* (2006.01)
*G01N 35/10* (2006.01)
*G06F 17/00* (2006.01)

(52) U.S. Cl.
CPC .......... *G06F 17/00* (2013.01); *G01N 35/00594* (2013.01); *G01N 35/00663* (2013.01); *G01N 2035/00881* (2013.01)

(58) Field of Classification Search
CPC ................. G01N 35/00594; G01N 35/00663
See application file for complete search history.

(56) References Cited

U.S. PATENT DOCUMENTS

| | | | |
|---|---|---|---|
| 5,892,458 | A | 4/1999 | Anderer et al. |
| 6,019,945 | A | 2/2000 | Ohishi et al. |
| 6,290,907 | B1 | 9/2001 | Takahashi et al. |
| 6,579,717 | B1 | 6/2003 | Matsubara et al. |
| 6,925,391 | B1 | 8/2005 | Pesce et al. |
| 2006/0265133 | A1 | 11/2006 | Cocks et al. |

FOREIGN PATENT DOCUMENTS

| | | |
|---|---|---|
| DE | 195 40 527 A1 | 5/1997 |
| EP | 0 732 591 A2 | 9/1996 |
| JP | 8-262029 A | 10/1996 |
| JP | 2003-4750 A | 1/2003 |
| JP | 2003-66051 A | 3/2003 |
| JP | 2003-279583 * | 10/2003 |
| WO | 2004/074845 A2 | 9/2004 |

\* cited by examiner

*Primary Examiner* — P. Kathryn Wright
(74) *Attorney, Agent, or Firm* — Mattingly & Malur, PC

(57) ABSTRACT

An automatic analyzer and an automatic analyzing system to identify samples and reagents used in the analyzer and members used in measurement of at least two objects in common: system reagents or buffer solution; sensor parts; probes; nozzles; chips; dispensing cups; tubes; ISE electrodes; detectors; deionized water; and waste, and to unify management of identification information thereof and a measurement result.

1 Claim, 6 Drawing Sheets

AUTOMATIC ANALYZER

This application is a continuation of U.S. patent application Ser. No. 11/514,185, filed Sep. 1, 2006, now U.S. Pat. No. 8,245,907 B2 issued on Aug. 21, 2012, the contents of which are hereby incorporated by reference into this application.

BACKGROUND OF THE INVENTION

1. Field of the Invention

The present invention relates to an automatic analyzer to perform qualitative and quantitative analysis on biological samples such as blood and urine, and particularly to an automatic analyzer having a function of easily examining a cause of data failure.

2. Description of the Related Art

In an automatic analyzer to perform qualitative and quantitative analysis on biological samples such as blood and urine, identification (ID) marks such as barcodes are attached on respective reagents and samples (specimens), and information of the reagents and samples is automatically registered in the analyzer by an ID mark reader, so as to prevent a mix-up of samples and use of a wrong reagent or a reagent for controlling accuracy (calibrator, control serum, etc.). The barcode attached on each reagent may include a lot number of the reagent and an analysis parameter or the like used to calculate a measurement value when analysis is performed by using the reagent. Such an automatic analyzer is disclosed in Patent Document 1 (JP, A 8-262029).

An analysis result of each sample is stored while being associated with the lot number of a reagent used in the analysis, so that which lot of reagent was used can be checked after the analysis.

SUMMARY OF THE INVENTION

The automatic analyzer is provided with ID information to identify standard samples (standard specimens) and reagents. However, consumables other than the samples and reagents are also used in analysis, for example, buffer solution, disposable nozzle chips to be attached on the top of a dispensing nozzle, dispensing cups, nozzles, tubes, ISE electrodes, and detectors.

These consumables have conventionally been believed not to affect an analysis result very much, and thus the conventional automatic analyzer does not have a function of identifying the lots of the consumables.

However, in the present circumstances where high analysis accuracy is required, even a slight deterioration of a tube may cause an abnormal measurement result. In that case, a lot of time is required to determine the cause of abnormality in [.] the conventional analyzer.

An object of the present invention is to provide an automatic analyzer having a function of immediately finding a cause of abnormality occurred in an analysis result.

In order to achieve the above-described object, the present invention has the following configuration.

According to an aspect of the present invention, there is provided an automatic analyzer including a storage unit for storing identification information attached to consumables used in measurement of two or more types of samples in common and a measurement result obtained by measuring the samples by using the consumables, the consumable identification information being associated with the measurement result of the sample.

The consumables may preferably include at least one selected from a group consisting of system reagents or buffer solution, sensor parts, probes, nozzles, chips, dispensing cups, tubes, ISE electrodes, detectors, and deionized water. The identification information may preferably be manufacture lot numbers assigned by respective consumables manufactures, but may be information that is arbitrarily given by a user in accordance with the time of purchase. The above-described "used in measurement of two or more types of samples in common" means that, for example, different sample are analyzed by using the same nozzle. The consumables are diversified ranging from those to be used for a long time (for more than a year), such as nozzles and tubes, to nozzle chips that are replaced after several measurement. However, the consumables are not limited as long as they are used in measurement of two or more types of samples.

Preferably, the automatic analyzer may further include a display unit for displaying a list of a measurement result determined to be abnormal and the identification information of consumables used in the measurement. "Displaying a list" means displaying a measurement result and types and identification information of consumables in a table. By seeing the list, the user can clearly recognize a relationship between consumables having the same identification information and the measurements performed by using the consumables.

The above-described configuration is not limited to one automatic analyzer, but may be applied to a system in which a plurality of automatic analyzers are connected through a server or data service center. In this case, if there exists a consumable used in measurements determined to be abnormal in common in one of the automatic analyzers, the identification information of the consumable is transmitted to the other automatic analyzers, and identification information is given to a result of analysis using the consumable specified by the identification information. That is, a warning that the consumables of this lot may have a failure and thus the use thereof should be avoided or that results of the measurement that have been done may have an error can be provided using an alarm warning unit.

Also, a data service center to manage information in which an analyzer is associated with identification information of consumables used in a plurality of items in the analyzer by using IDs (identifiers) may be provided. The analyzer may include a unit to store a measurement result in the analyzer and identification information of consumables in the analyzer; and a unit to transmit the association information to the data service center connected thereto through a network. The data service center may include a unit to receive the association information from the analyzer through the network; and a unit to store the received association information in a database provided in the center. That is, the management of consumables in units of lots can be performed not only in a hospital but also in units of local areas, prefectures, or countries.

In the automatic analyzer, a cause of a problem which occurred during measurement can be swiftly pursued and analyzed. As a result, countermeasures against the problem can be estimated.

DESCRIPTION OF THE PREFERRED EMBODIMENTS

Figure 1:
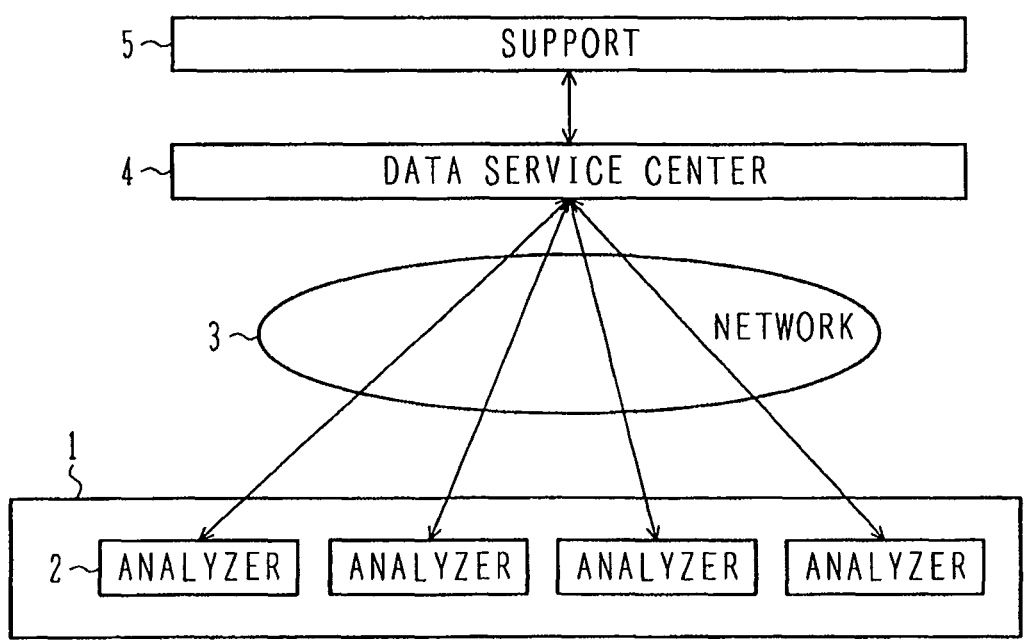
FIG. 1 is a conceptual view of a system according to the present invention.

First, a configuration of an automatic analyzer according to the present invention is described with reference to FIG. 5 by using a pipettor-type analyzer as an example. In reaction containers 76b arranged in a reaction site 35B of the analyzer, reaction of samples and reagents regarding a predetermined analysis item progresses. A sample rack 31 is placed at a pipetting position, a specified sample is pipetted by a pipette nozzle of a sample pipettor 78b, and a predetermined amount of the sample is ejected into the reaction container 76b. The sample pipettor 78b includes a sampling pipettor pump 77b. The reaction site 35B is kept at a constant temperature (e.g. 37° C.) by a thermostatic liquid supplied from a thermostatic chamber 40.

Figure 5:
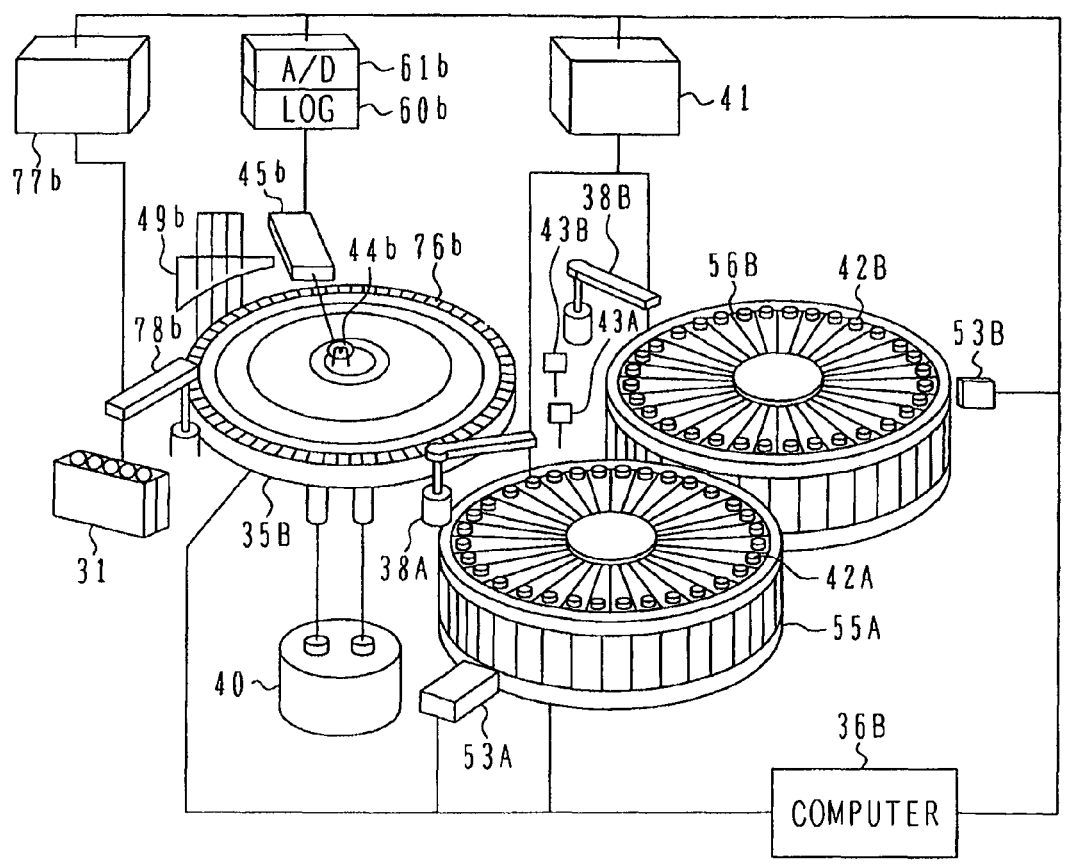
FIG. 5 shows an example of a configuration of an automatic analyzer according to the present invention.

A pipettor-type reagent supplying unit 56 of the analyzer shown in FIG. 5 includes two reagent disks 55A and 56B for first and second reagents. Reagent bottles 42A and 42B containing various reagents prepared for many analysis items are attached with barcodes serving as reagent ID information on their outer walls. After the reagent bottles 42A and 42B have been placed in the reagent disks 55A and 56B, the reagent ID information attached on each reagent bottle is read by a barcode reader 53A or 53B, and the read information is stored in a storage unit 7 together with the set position on the reagent disk of the reagent bottle, a corresponding analysis item, and the number assigned to the analyzer in which the reagent bottle is set. Reagent pipettors 38A and 38B include a reagent pipettor pump 41 connected to each pipette nozzle that can rotate and move vertically.

The array of the reaction containers 76b in which samples have been pipetted is rotated, a predetermined amount of first reagent is pipetted by the reagent pipettor 38A from the reagent bottle 42A positioned at a pipetting position in accordance with an analysis item, and the first reagent is ejected into the reaction container 76b placed at a reagent adding position. After the content has been stirred by a stirring mechanism 43A at a stirring position, the array of the reaction containers is conveyed a plurality of times. When the reaction container 76b reaches a second reagent adding position, the reagent pipettor 38B pipettes the second reagent from the reagent bottle 42B positioned at a pipetting position in accordance with an analysis item and ejects the reagent into the reaction container. Then, the content in the reaction container is stirred by a stirring mechanism 43B. Then, a light flux from a light 44b passes through the reaction container 76b in accordance with the rotation of the array of the reaction containers, and the light flux passed through the reaction liquid in the reaction container 76b is detected by a multiwavelength photometer 45b. A signal having a wavelength corresponding to the analysis item is processed by a logarithmic converter 60b and an A/D converter 61b controlled by a computer 36B on the analyzer side, and a digital signal is transmitted to a computer 36B for entire control. The reaction container 76b after measurement is cleansed by a cleansing mechanism 49b and is reused.

In the above-described automatic analyzer, consumables include those to be refilled, exchanged, or disposed by a user, for example, buffer solution; chips; dispensing cups; nozzles; tubes; ISE electrodes; detectors; deionized water; and waste.

When ID information is to be applied (identification) to the consumables, the following methods can be used. For example, a barcode issuing unit is provided on the analyzer and IDs of the respective consumables are stored in the analyzer by radiation, as in conventional registration of reagent information. Alternatively, ID lattices (chips or IC tags) may be embedded in the consumables in advance and the information may be provided to the analyzer wirelessly.

Figure 2:
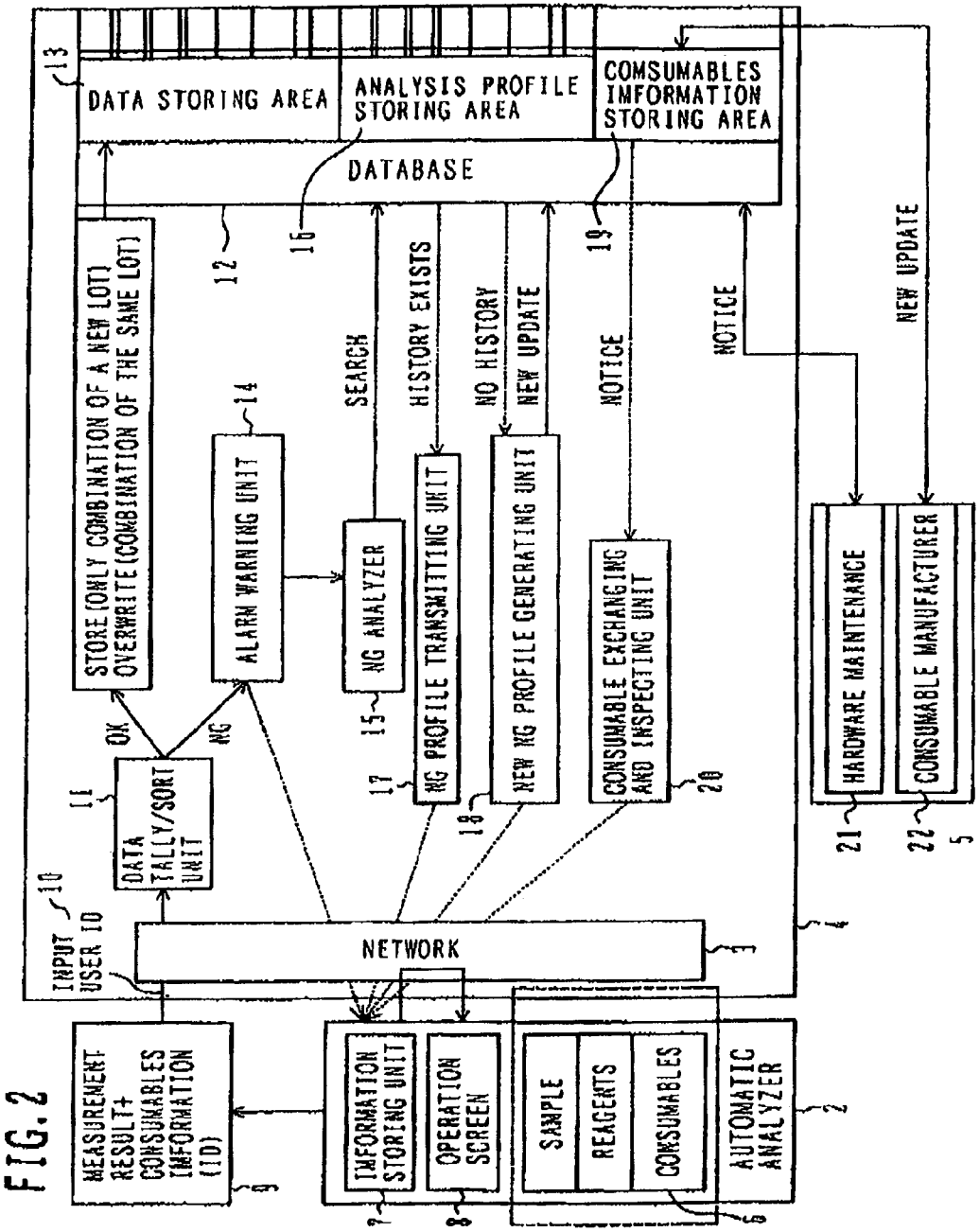
FIG. 2 shows a schematic configuration of an analyzer and a data service center according to the present invention.

Hereinafter, an embodiment of the present invention is described with reference to FIG. 2. An abnormal measurement result caused by a consumable can be instantaneously determined by displaying a measurement status and consumables information, received from an alarm warning unit 14, in an operation screen 8 during measurement. Information 9 including a measurement result and consumables information associated with each other is transmitted to a data service center 4 after authentication in a user ID authenticating unit 10. Then, the information 9 including the measurement result and the consumables ID information used in the measurement is tallied and sorted by a tally/sort unit 11, several steps are preformed, and management of the data is unified. The data is managed while being stored in a data storing area 13 of a database 12 in the service center 4 in units of facilities, and respective measurement results are constantly stored. If data of a measurement result is different from existing data, the data is transmitted from the data tally/sort unit, through the alarm warning unit to an NG analyzer 15, where the cause is analyzed. In the analysis, an analysis profile storing area 16 is searched for the same pattern. If a history exists, NG profile information is transmitted to an information storing unit 7 in the analyzer and is stored in the analyzer so that the same symptom does not occur again. If the same pattern is not found, a new NG profile is generated by a new NG profile generating unit 18 on the basis of the analysis profile. The generated NG profile is written in an analysis profile storing area 16 and is transmitted to the information storing unit 7 in the analyzer so as to be stored therein.

First Embodiment

<Method for Registering ID and Method for Associating Measurement Result>

A trouble due to a consumable member used in common to measure at least two objects is explicitly notified to a user, who is then encouraged to take countermeasures.

Figure 3:
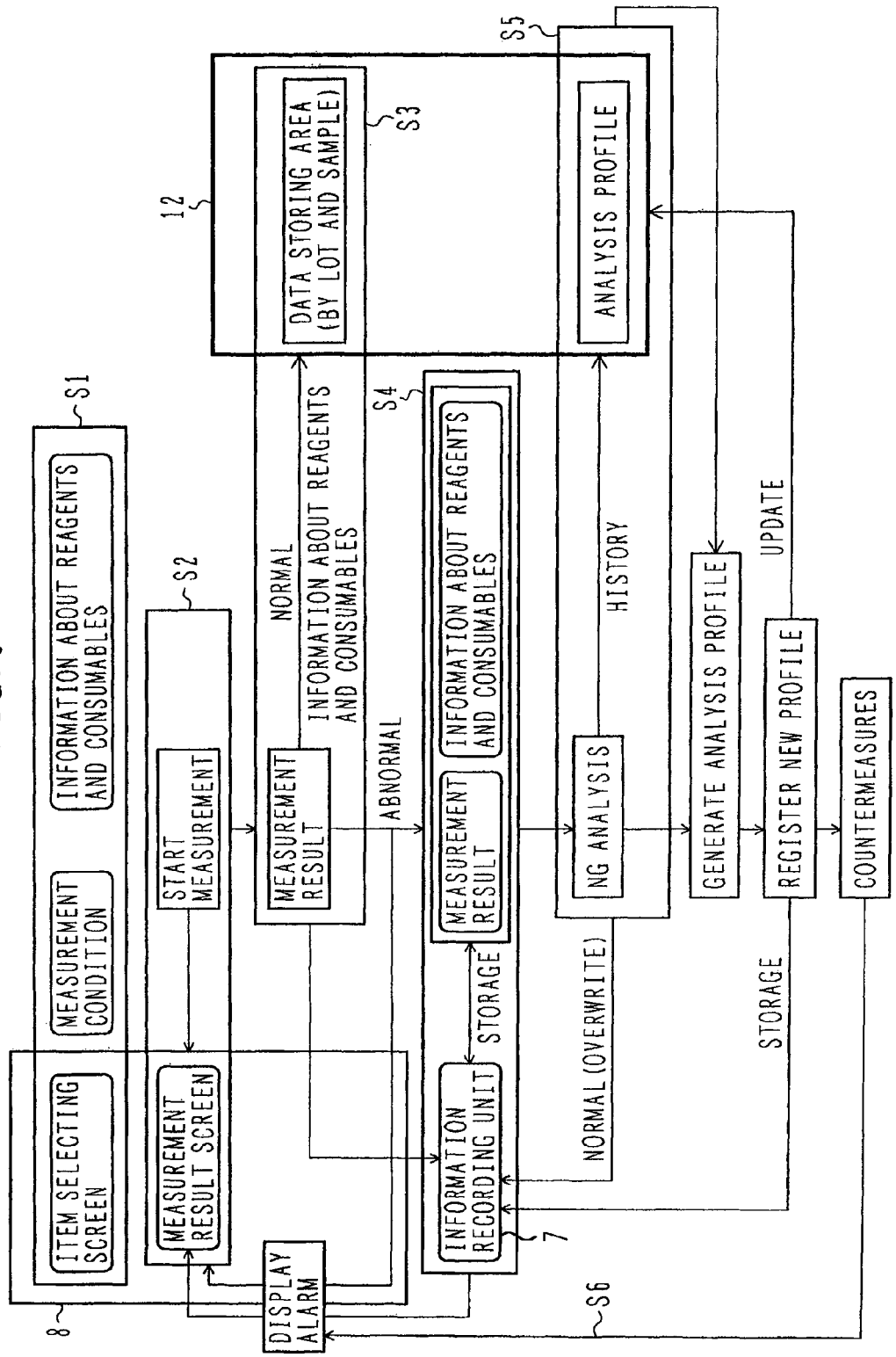
FIG. 3 shows a method for registering an ID and a method for associating a measurement result according to the present invention.

An example is described by using a system reagent with reference to FIG. 3.

First, reagents are registered in step S1. A handy barcode reader is attached on the analyzer so that lot information of system reagents can be easily registered. Alternatively, identifiers Oa chips or IC tags) are embedded in consumables, information thereon is read wirelessly, and system reagent information is registered in the analyzer. In order to limit item reagents, 1) a standard range of a general sample in each item is input; and 2) an expected value (desired value) of each sample (Control-Calibration) is input. Then, lot information is recorded or stored. Information about consumables used in common to measure at least two objects is stored by item, measurement condition, and time, and the information is stored in the analyzer.

In step S2, measurement is performed and a measurement result is obtained.

In step S3, the system reagent used in the measurement is specified and is stored, and it is determined whether association is necessary in the measurement result. Also, 1) it is determined whether the sample is a control sample or a calibrator sample, and 2) measurement is performed a plurality of times on a specimen in which the sample is a general sample.

Then, after an average of measurement values has been obtained, it is determined whether the average exceeds the expected value of the specimen.

If the measurement result is NG, the process proceeds to step S4, where associated lot information of the measurement result requiring association is searched for.

Figure 6:
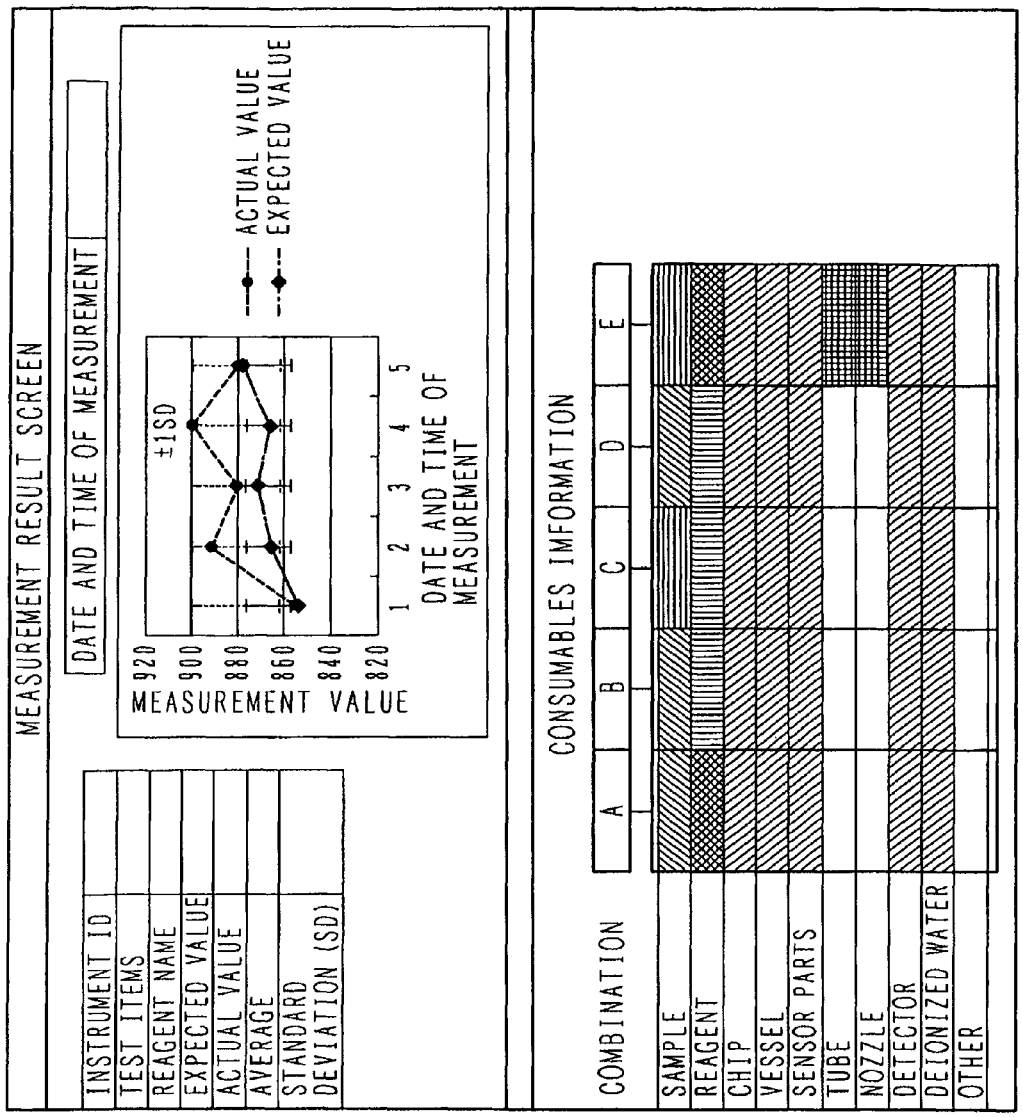
FIG. 6 shows a screen displaying a measurement result and information about consumables according to the present invention.

In step S5, the associated lot information is displayed on the operation screen while being associated with the measurement result (5). An example of the screen displayed is shown in FIG. 6. In addition to information about a measuring instrument; date and time of measurement; and a measurement item, information about respective consumables are listed on the screen. Accordingly, abnormality caused by a combination of consumables used in the measurement can be determined. When abnormality occurs, the abnormal part blinks so that the user can recognize a part to be inspected. Incidentally, measurement results obtained by using different combinations of consumables can be compared and the comparison result can be held as reference data in the device. That is, a measurement result and information about consumables used in the measurement are displayed together on the operation screen.

Finally, in step S6, causes of the abnormality are estimated on the basis of the association, possible causes are ranked, and countermeasures against each of the estimated causes are displayed on the operation screen.

In this way, steps S1 to S6 are performed, so that registration of IDs and association of a measurement result complete.

Second Embodiment

<Relationship Between Data Service Center and Analyzers>

Hereinafter, the definition of the data service center in the present invention is described with reference to FIG. 2.

The data service center 4 connects to a plurality of analyzers 2 through a network 3 and serves as an agency to store measurement results in the respective analyzers and information about the consumables used. The center 4 is provided with the database 12 to accumulate the information 9 including the measurement results obtained from the analyzers 2 and ID information of the consumables used. The database 12 receives the information 9 from each of the analyzers 2. The information 9 received by the database 12 is stored in units of users. Also, the information 9 is stored while being sorted by analyzer, analysis item, and information about consumables. A user can access history information by inputting his/her user ID in the user ID authenticating unit 10. Also, an average of measurement values received from the automatic analyzers 2 is calculated, measurement results and information about consumables in a plurality of combinations are statistically analyzed, and tendency and pattern are transmitted to the analyzers so as to be stored therein. If an abnormal measurement result due to a consumable is generated, a method for avoiding the trouble is distributed or transmitted through the network.

Third Embodiment

<Method for Identifying and Determining Consumables at Data Failure>

Figure 4:
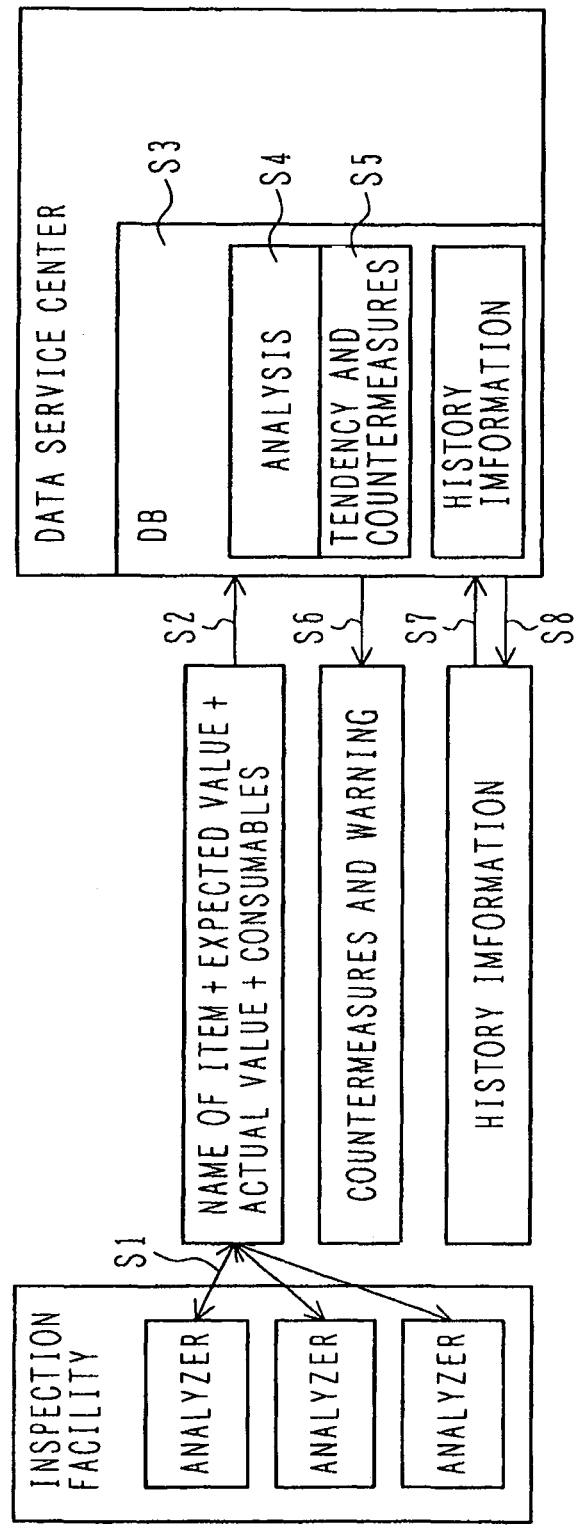
FIG. 4 shows a method for identifying and determining consumables when data failure occurs according to the present invention.

A method for identifying and determining consumables at data failure is described with reference to FIG. 4.

In step S1, the information 9 including measurement results associated with the name of an item, an expected value, an actual value, and consumables, is transmitted from an inspection facility 1 to the data service center 4 through the network 3.

In step S2, the database 12 in the center 4 receives the information 9 from the analyzers in each inspection facility.

In step S3, the measurement results and information about consumables are accumulated in the database 12 in the center 4.

In step S4, a common point in the plurality of analyzers is searched for and is analyzed.

In step S5, countermeasures are taken on the basis of the information found in step S3.

In step S6, the center 4 transmits the countermeasures and warning, using the alarm warning unit 14, to the analyzers 2. In step S7, history information stored in the data storing area 13 in the center 4 is browsed.

Finally, in step S8, the analyzers 2 receive the countermeasures and warning from the alarm warning unit, as transmitted in step S6 and the history information browsed in step S7.

By performing the above-described steps S1 to S8, the method for identifying and determining consumables can be performed when data failure occurs. By unifying management of measurement results obtained from analysis and consumables used in the measurements by using identifiers, the cause of a trouble can be specified even if the trouble occurs. Furthermore, countermeasures against the trouble can be determined.

Fourth Embodiment

Analysis Program

NG results transmitted from a plurality of inspection facilities 1 to the data service center 4 are tallied up and the statistics are calculated.

The statistics are calculated by using an analyzing tool in each of (1) overall tendency; (2) weekly report; (3) monthly report; (4) annual report; (5) lot number; and (6) measurement item. The calculated statistics are stored in the analysis profile area 16 in the database 12 provided in the service center 4.

If a measurement result does not match that stored in the information storing unit 7 in the analyzer 2, the measurement result is transmitted to the data service center 4 and the analysis profile storing area 16 is automatically searched.

If a measurement result matches a result example stored in the information storing unit 7 in the analyzer 2, the measurement result is transmitted to the data service center 4 and is stored in the data storing area 13 in the database 12 provided in the service center 4.

If it is not sure whether a data failure is due to measurement or due to a lot, measurement is performed again by using another lot or another reagent.

If data failure is determined in the analyzer, information thereof is stored in the system so that the data is automatically masked if the data is to be used.

What is claimed is:

1. An automatic analyzer system comprising:
plural kinds of consumables used in common to measure at least two samples, said plural kinds of consumables including at least two consumables selected from a group of consumables including nozzle chips, dispensing cups, nozzles, tubes, ISE electrodes, and detectors, each consumable including an identifier including consumable identification information;
a plurality of automatic analyzers, each automatic analyzer including:
a means for reading the consumable identification information;
an information storing unit for storing consumable identification information of consumables used in common to measure at least two kinds of samples read by the means for reading, and for storing measurement result values of each of a plurality of samples measured in each automatic analyzer by using said consumables;

a controller having a program configured to execute the steps of:

associating the consumables identification information with said measurement results for each of said at least two kinds of samples in each of the plurality of automatic analyzers, and transmitting the association information to a data service center connected thereto through a network and wherein the data service center is connected to each of said plurality of automatic analyzers through a network, said data service center including:

an information storing unit for storing information associated with the name of a sample, an expected measurement result value, an actual measurement result value and consumable identification information associated with measurement results of each of the plurality of samples measured by using said plurality of consumables in each of said automatic analyzers and sent to said data service center from each of said plurality of automatic analyzers through the network, an alarm warning unit for communicating alarm information to each of said plurality of automatic analyzers on the basis of said plurality of consumable identification information of said consumables when there is a consumable which is used in common in measurements and which is determined to be abnormal in one automatic analyzer, the alarm information being transmitted by the data service center to other ones of the plurality of automatic analyzers using the consumable determined to be abnormal, said data service center further having a controller including a program configured to execute the steps of:

receiving and storing the information associated with the name of a sample, the actual measurement result value of the sample, and the consumable identification information for the plurality of consumables from one of the plurality of automatic analyzers used in the measurement;

searching said received information stored in the data service center information storing unit to find consumables used to measure at least two kinds of sample whose actual measurement result is judged to be abnormal in one of the plurality of analyzers;

transmitting alarm information to each of the other ones of the plurality of automatic analyzers on the basis of said plurality of consumable identification information of said consumables when there is a consumable which is used in common in measurements and which is determined to be abnormal in one automatic analyzer; and constructing a countermeasure for the cause of the abnormality and transmitting the countermeasure to the one of the plurality of automatic analyzers transmitting the abnormal measurement result.

\* \* \* \* \*